United States Patent
Brown, III et al.

(10) Patent No.: US 6,424,862 B1
(45) Date of Patent: Jul. 23, 2002

(54) IONTOPHORESIS ELECTROPORATION AND COMBINATION PATCHES FOR LOCAL DRUG DELIVERY TO BODY TISSUES

(75) Inventors: Charles L. Brown, III, Atlanta, GA (US); Neville Crawford, Wetherby (GB)

(73) Assignee: GMP Drug Delivery, Inc., Fort Lauderdale, FL (US)

( * ) Notice: Subject to any disclaimer, the term of this patent is extended or adjusted under 35 U.S.C. 154(b) by 0 days.

(21) Appl. No.: 09/502,108

(22) Filed: Feb. 10, 2000

(51) Int. Cl.[7] .................................................. A61N 1/30
(52) U.S. Cl. ........................ 604/20; 604/174; 604/501
(58) Field of Search ........................... 604/19, 20, 46, 604/174, 289–291, 501

(56) References Cited

U.S. PATENT DOCUMENTS

| | | |
|---|---|---|
| 4,141,359 A | 2/1979 | Jacobsen et al. |
| 4,383,529 A | 5/1983 | Webster |
| 4,474,570 A | 10/1984 | Ariura et al. |
| 4,640,689 A | 2/1987 | Sibalis |
| 4,764,164 A | 8/1988 | Sasaki |
| 4,842,577 A | 6/1989 | Konno et al. |
| 4,919,648 A | 4/1990 | Sibalis |
| 4,921,475 A | 5/1990 | Sibalis |
| 4,950,229 A * | 8/1990 | Sage, Jr. .................... 604/20 |
| 5,002,527 A * | 3/1991 | Reller et al. ................ 604/20 |
| 5,006,108 A | 4/1991 | LaPrade |
| 5,013,293 A | 5/1991 | Sibalis |
| 5,019,034 A | 5/1991 | Weaver et al. |
| 5,047,007 A | 9/1991 | McNichols et al. |
| 5,084,006 A | 1/1992 | Lew et al. |
| 5,087,240 A | 2/1992 | Sibalis |
| 5,088,977 A | 2/1992 | Sibalis |
| 5,135,478 A | 8/1992 | Sibalis |
| 5,160,316 A | 11/1992 | Henley |
| 5,163,899 A | 11/1992 | Sibalis |
| 5,207,752 A | 5/1993 | Sorenson et al. |
| 5,312,325 A | 5/1994 | Sibalis |
| 5,328,452 A | 7/1994 | Sibalis |
| 5,328,453 A | 7/1994 | Sibalis |
| 5,328,454 A | 7/1994 | Sibalis |
| 5,336,168 A | 8/1994 | Sibalis |
| 5,372,579 A | 12/1994 | Sibalis |
| 5,405,317 A | 4/1995 | Myers et al. |
| 5,415,629 A | 5/1995 | Henley ....................... 604/20 |
| 5,423,739 A | 6/1995 | Phipps et al. |
| 5,464,386 A * | 11/1995 | Hofmann ..................... 604/20 |
| 5,618,265 A | 4/1997 | Myers et al. |
| 5,620,580 A | 4/1997 | Okabe et al. |
| 5,645,526 A | 7/1997 | Flower |
| 5,688,231 A | 11/1997 | Flower |
| 5,688,232 A | 11/1997 | Flower |
| 5,693,024 A | 12/1997 | Flower |
| 5,713,846 A | 2/1998 | Bernhard et al. |
| 5,738,647 A | 4/1998 | Bernhard et al. |
| 5,817,044 A | 10/1998 | Evers et al. |
| 5,823,989 A * | 10/1998 | Ostrow ....................... 604/20 |
| 5,830,175 A | 11/1998 | Flower |
| 5,857,994 A | 1/1999 | Flower |
| 5,876,368 A | 3/1999 | Flower |
| 5,895,369 A | 4/1999 | Flower |
| 5,968,006 A | 10/1999 | Hofmann |
| 5,983,132 A | 11/1999 | Millot et al. |
| 5,983,133 A | 11/1999 | Garde et al. |
| 6,009,345 A * | 12/1999 | Hofmann ..................... 604/20 |
| 6,302,874 B1 * | 10/2001 | Zhang et al. ................ 604/501 |

* cited by examiner

Primary Examiner—J. Casimer Jacyna
(74) Attorney, Agent, or Firm—Sutherland Asbill & Brennan LLP

(57) ABSTRACT

Patch-based devices for enhancing the local delivery of drugs, pharmaceuticals, plasmids, genes, and other agents into the tissues of the living body. The patch devices provide an electrical driving force that can increase the rate of migration of drugs and other therapeutic agents out of a polymer matrix into body tissues and cells using iontophoresis only, electroporation only, or combined iontophoresis and electroporation. The two procedures may be applied sequentially in any order without removing or repositioning the patch.

20 Claims, 3 Drawing Sheets

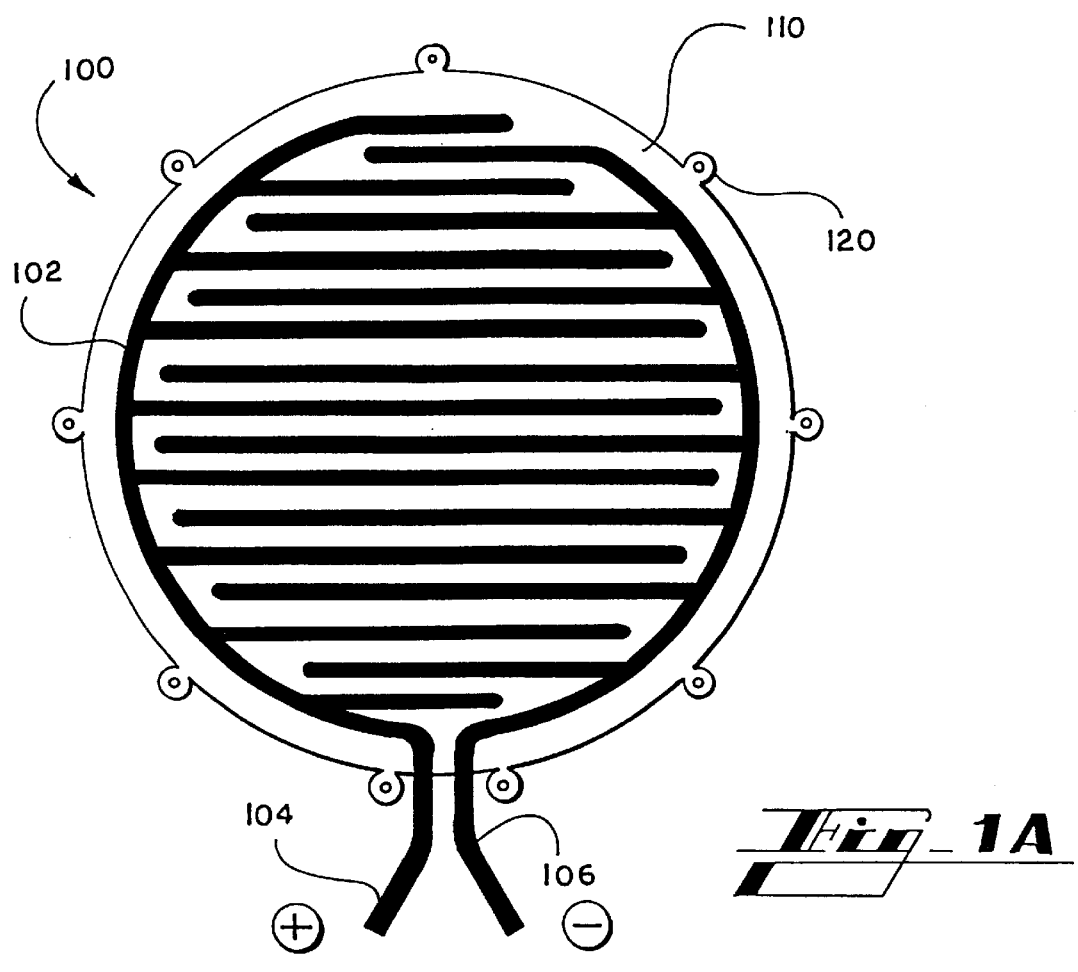
Fig_1A
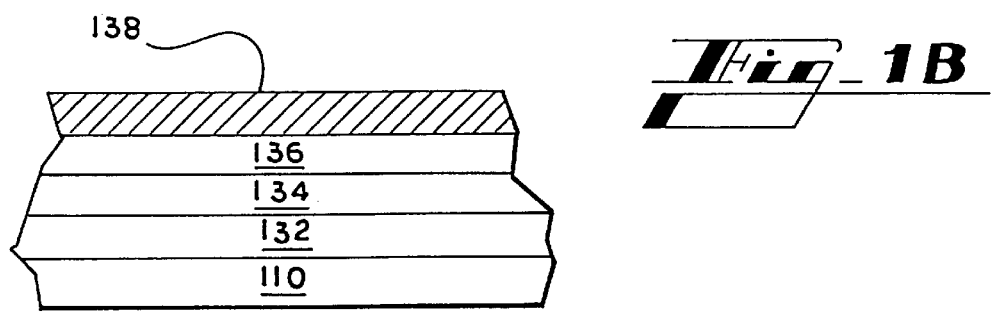
Fig_1B

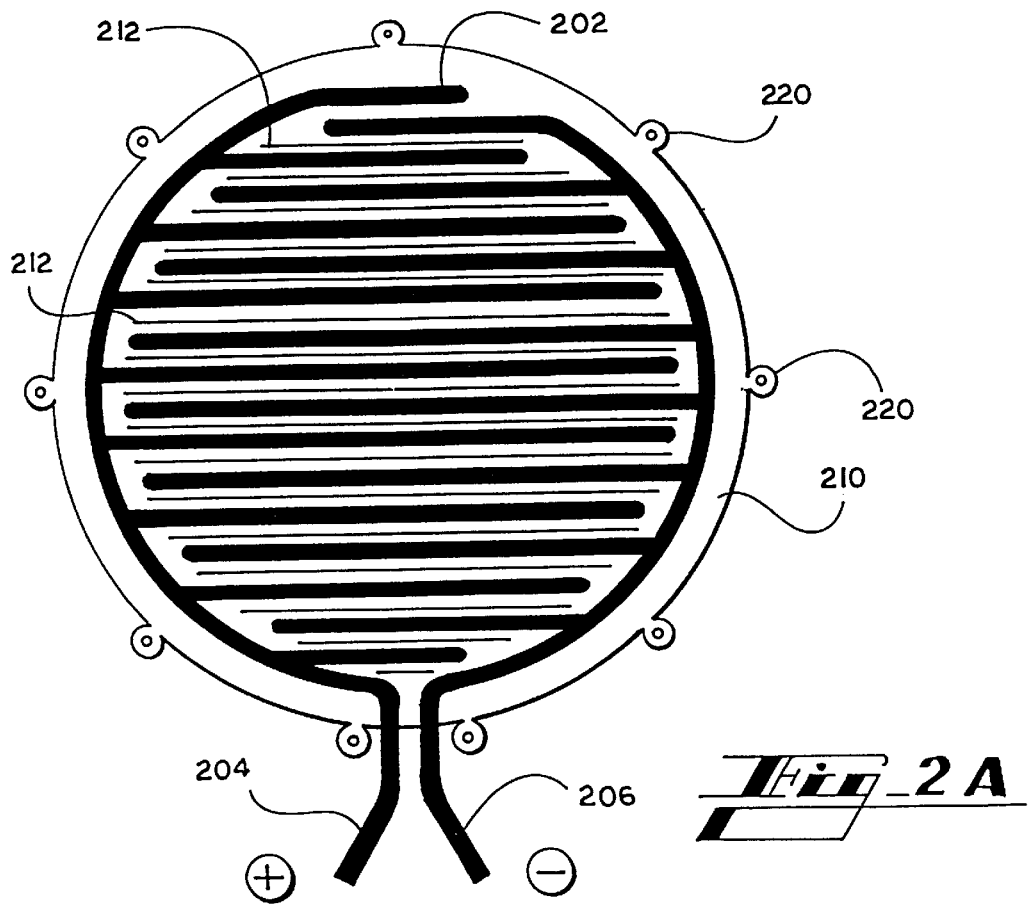
Fig_2A
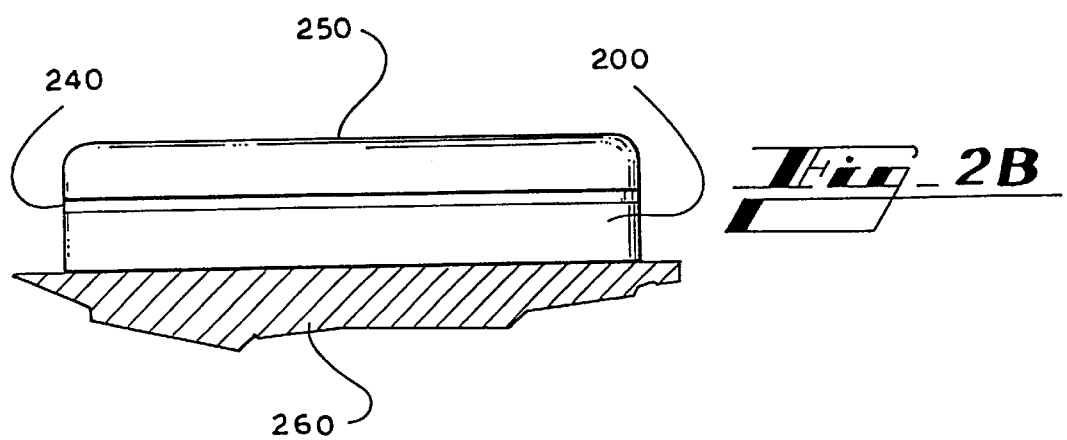
Fig_2B

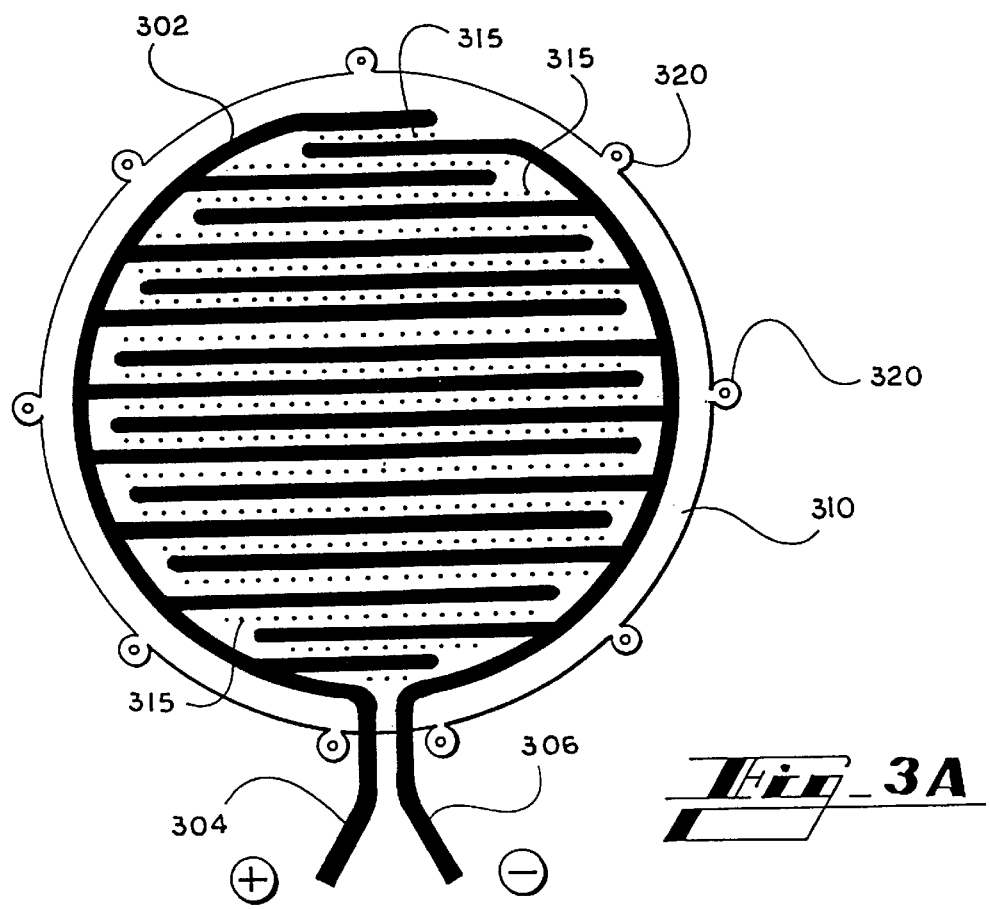
Fig_3A
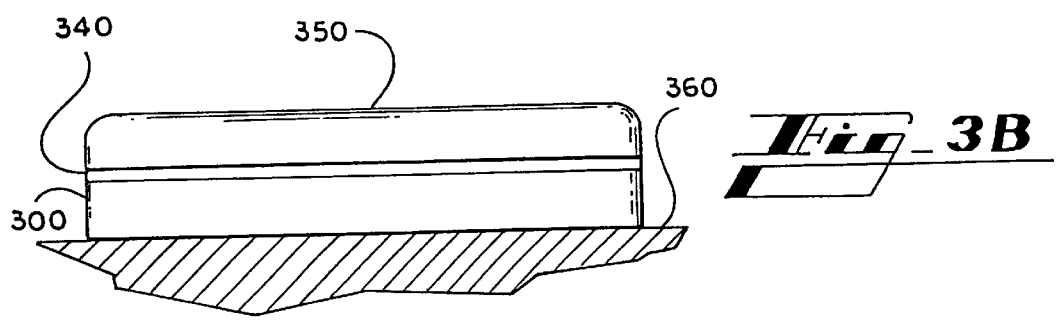
Fig_3B

US 6,424,862 B1

IONTOPHORESIS ELECTROPORATION AND COMBINATION PATCHES FOR LOCAL DRUG DELIVERY TO BODY TISSUES

FIELD OF THE INVENTION

The present invention relates in general to devices for enhancing the local delivery of drugs, pharmaceuticals, plasmids, genes, and other agents into the tissues or cells of the living body. In particular, the present invention relates to patch-based devices which provide an electrical driving force that can increase the rate of migration of drugs and other therapeutic agents out of a polymer matrix into body tissues and cells using iontophoresis only, electroporation only, or combined iontophoresis and electroporation. The two procedures may be applied sequentially in any order without removing or repositioning the device.

BACKGROUND OF THE INVENTION

Many different treatment agents, such as medicines, are generally administered to the body by various methods, such as topical application, oral ingestion, intravascular, intramuscular or parenteral injection and, less commonly, by aerosol insufflation and transdermal iontophoresis and electroporation. In all of these treatments there is an immediate dilution effect greatly reducing the concentration to which the target tissues or cells are exposed. Also, medicines administered by these systems may be more vulnerable to processes such as metabolic degradation, inactivation by binding to plasma proteins or accelerated clearance from the body. These processes adversely affect the drug's concentration and residence time in the target tissues and reduce its therapeutic efficacy.

Most of the above modes of drug administration also expose non-target tissues, i.e. those that do not require treatment, to the action of the drugs, with the consequent risk of serious side effects. It is this risk towards non-target tissues that reduces a drug's efficacy by restricting systemic concentrations to a threshold level above which the side effects would become unacceptable.

Local drug delivery procedures can obviate some of the metabolic breakdown, early clearance and side effect problems affecting efficacy by presenting therapeutic concentrations of a drug only to the target site, minimizing effects upon non-target tissues. The reduction in quantity of a drug required can also result in lower treatment costs.

Recognition of the advantages for local delivery strategies has stimulated the development of a number of catheter-based and patch-based delivery devices which apply drugs a directly to the body tissues at certain locations, often to sites that would be otherwise inaccessible without surgery. However, if the specific target for an agent is intracellular, simple local application of the drug, followed by its passive diffusion into tissues, does not facilitate movement of the drug across cell surface membrane barriers into cytoplasmic compartments. Diffusion away from the target cells occurs and high extracellular concentrations are rarely sustained long enough to mediate significant passage into the cells. Some drugs penetrate intact cell membranes by diffusion very poorly and may require specific carriers or bulk transport by a phagocytic or pinocytic mechanism to penetrate the cell membrane. However, these natural transport systems operate poorly, or not at all, when the tissues are affected by disease.

Iontophoretic catheters and patches have been explored in some animal angioplasty studies to provide an electrical driving force for movement of a drug into tissues. This technique requires that the agent to be delivered carries an electrical charge under the local physiological pH conditions. While iontophoresis appears to enhance the delivery of drugs into body tissues, it has been shown in transdermal iontophoresis ("TDI"), that the migration of drugs through skin predominantly occurs via extracellular pathways (sweat glands and hair follicle channels) where the current densities are much higher than elsewhere. This preferential channel movement may be favorable towards providing high drug concentrations in the skin capillary bed and onward into the circulation. However, if it is a feature of other tissues, such as blood vessels and other organ surfaces, the delivery of drugs to cellular targets will be of low efficacy.

Additionally, these iontophoretic patches are only used for transdermal applications. These patches typically use an adhesive to adhere the device to the skin while iontophoresis is used to cause the migration of the drugs. Uses of the device on internal tissues or on the eye are not possible as the adhesive will not effectively hold the device, or may be detrimental to the surface to be treated.

Additionally, the transdermal patches have only a set amount of medicament that may be delivered before the patch must be removed and recharged or replaced, limiting the possible uses of the device.

Accordingly, what is needed are devices for delivering treatment agents to specific locations, especially intracellular locations, in a safe and effective manner. These devices would deliver the agents such that effective amounts may be delivered without endangering tissues or cells in non-target areas. Additionally, the devices would be capable of being placed inside the body and held in place while also being capable of having additional medicament be added to the device to permit the patch to be used for an indefinite period of time without the need to be removed and/or replaced.

SUMMARY OF THE INVENTION

The present invention is directed to devices for enhancing the local delivery of treatment agents into the tissues or cells of the living body. These devices are designed to target certain tissue and cell locations and deliver the treatment agents directly to those locations, while minimizing any effects on non-targeted tissues and cells. Additionally, these devices are designed to be placed inside the body and held in place while also being designed to be used for an indefinite period of time without the need to be removed and/or replaced.

In particular, the present invention relates to patch-based devices which provide an electrical driving force that can increase the rate of migration of drugs and other therapeutic agents out of a polymer matrix or other carrier mechanism into body tissues and cells using iontophoresis only, electroporation only, or combined iontophoresis and electroporation. A preferable approach may be for electroporation to be applied to permeabilize the cells after pre-iontophoresis of the agent into the tissues. Preferably, the device is able to perform the two procedures sequentially without repositioning of the device. The patch is designed to maintain a high concentration of drug in the tissue extracellular spaces (e.g. by iontophoresis) such that the subsequent creation of transient pores in cell surface membranes by electroporation pulses results in greatly improved intracellular delivery of the treatment agent.

Alternatively where a tissue, organ or solid tumor has an impenetrable margin or denser peripheral zone inhibitory to iontophoretic migration, the patch may be used to first to perturb such barrier regions with electroporation pulses to facilitate diffusion or iontophoretic migration of the drug into the interior of the tissue. Intracellular penetration may then be enhanced by the application of electroporation pulses. Such a protocol may be particularly advantageous for the delivery of larger molecular weight agents, antibody fragments and gene constructs.

One mode of intracellular targeting, which is particularly applicable to therapeutic agents that do not readily pass through cell membranes, is electroporation. In electroporation, cell membranes can be rendered transiently permeable by the application of electrical fields of short pulse width (microseconds to milliseconds). With appropriate parameters, including time, sequence of pulse, pulse width and field strength, the cell membranes will reseal to their former structural and functional integrity.

The present invention is particularly applicable to the local delivery of drugs during interventional cardiology procedures such as angioplasty and stent implantation. Other applications include use during open heart surgical procedures, for application of drug or therapeutic proteins to the heart or pericardial surface or for systemic or local drug delivery, such as delivery of anesthetic agents to achieve nerve block for minimally invasive CABG surgery. Cutaneous combined iontophoresis and electroporation could also be achieved with the patch. Also, the patch may be used on or around the eye for ocular procedures. Finally, application of the patch to other tissues, such as tumors, could help facilitate delivery of chemotherapeutic agents. Unlike electrical drug delivery catheters, the electrodes in the present inventions are part of a patch. This device allows body tissues not located within or near a body vessicle to be treated. The patch may be used on the skin or eyeball, but is especially useful for placement directly on internal tissues or organs, such as the heart, liver or pancreas, or specifically sited on areas of cancer growth. The patch-based devices of the present invention have much more flexibility in where they are able to be used.

Accordingly, it is an object of the present invention to provide devices for electrically enhancing the local delivery of drugs, pharmaceuticals, plasmids, genes, and other agents.

It is another object of the present invention to provide devices for the local delivery of treatment agents into the tissues or cells of the living body.

It is another object of the present invention to provide devices which use iontophoresis and/or electroporation to enhance the local delivery of treatment agents.

It is another object of the present invention to provide devices which are able to deliver treatment agents to specific tissues and cells without endangering non-targeted tissues and cells.

These and other objects, features and advantages of the present invention will become apparent after a review of the following detailed description of the disclosed embodiments and the appended claims.

BRIEF DESCRIPTION OF THE DRAWINGS

FIGS. 1a and 1b detail a top-view and a cross-sectional view, respectively, of an iontophoresis/electroporation patch-based device according to a first embodiment of the present invention.

FIGS. 2a and 2b detail a top-view and a cross-sectional view, respectively, of an iontophoresis/electroporation patch-based device according to a second embodiment of the present invention.

FIGS. 3a and 3b detail a top-view and a cross-sectional view, respectively, of an iontophoresis/electroporation patch-based device according to a third embodiment of the present invention.

DETAILED DESCRIPTION

The present invention is directed to devices for electrically enhancing the local delivery of treatment agents, such as drugs, pharmaceuticals, plasmids, genes, and other agents, into the tissues or cells of the living body. These devices are constructed and arranged to target certain tissue and cell locations and deliver the treatment agents directly to those locations, while minimizing any effects of the treatment agents on non-targeted tissues and cells.

In particular, the present invention relates to patch-based devices which provide an electrical driving force that can increase the rate of migration of drugs and other therapeutic agents out of a polymer matrix or other drug reservoir into body tissues and cells using iontophoresis only, electroporation only, or combined iontophoresis and electroporation. In certain situations, a preferable approach is for electroporation to be applied to permeabilize the cells after pre-iontophoresis of the treatment agent into the tissues. Preferably, the patch is able to perform the two procedures sequentially without repositioning of the patch. Even more preferably, the patch is designed to maintain a high concentration of drug in the tissue extracellular spaces (e.g. by iontophoresis) such that the subsequent creation of transient pores in cell surface membranes by electroporation pulses results in greatly improved intracellular delivery of the treatment agent.

The design, size and shape of the patches of the present invention may vary depending on the treatment agent to be delivered and the place into which the agent is to be delivered. However, the devices preferably include a reservoir which is capable of holding the drug to be delivered such that the drug may be added over a period of time, or even a plurality of different drugs may be used sequentially to treat the targeted tissues or cells. These reservoirs may also be rechargeable with additional or different treatment agents such that treatment of the target tissue may occur for extended periods of time. The reservoirs are preferably located on the back of the patch device such that the medicament passes through the patch material to the tissue to be treated. Since the electrodes are in contact with the skin and the patch is located on the other side of the patch away from the tissue to be treated, it is easier to recharge the reservoir with additional medicament or a different medicament, depending upon the desired protocol. By using rechargeable reservoirs, the patch device is capable of being implanted within an individual's body and used for extended periods of time.

The present invention allows for the enhancement of drug delivery on any bodily tissue or cell, for example, the eye, the heart, or any other organ, or even directly on cancer cells located anywhere in the body. The drug delivery may be carried out during another surgical procedure or as the only procedure.

For some treatment protocols, simple iontophoretic enhancement of local drug delivery may suffice. However, for others, such as cancer chemotherapy, electroporation of the cells in a particular region of tissue would be used to facilitate the intracellular penetration of a cytotoxic agent, such as bleomycin, present in the systemic circulation. Providing highly localized doses of a drug to target cells in this way may avoid exceeding the systemic concentration threshold where side effects become a serious problem.

For localized drug delivery to tissues in vivo, the use of both iontophoresis and electroporation procedures in sequence may be performed. For a sequential process, a drug would be delivered from the patch into the tissue by pre-iontophoresis to give a high concentration of the treatment agent in the extracellular space. The iontophoresis would be followed immediately by electroporation pulsing to permeabilize the membranes of cells within the tissue. A rapid gradient-driven diffusion of the treatment agent into the transiently permeabilized cells would facilitate targeting of the agent to intracellular elements and metabolic pathways at a concentration that is therapeutically effective. A sequence of alternate iontophoretic and electroporation pulses may be an appropriate treatment modality for certain tissues to optimize drug penetration and intracellular targeting. One of the patch embodiments discussed herein is capable of performing the sequential process without repositioning of the patch.

As used herein, the term "iontophoresis" means the migration of ionizable molecules through a medium driven by an applied low level electrical potential. This electrically mediated movement of molecules into tissues is superimposed upon concentration gradient dependent diffusion processes. If the medium or tissue through which the molecules travel also carries a charge, some electro-osmotic flow occurs, However, generally, the rate of migration of molecules with a net negative charge towards the positive electrode and vice versa is determined by the net charge on the moving molecules and the applied electrical potential. The driving force may also be considered as electrostatic repulsion. Iontophoresis usually requires relatively low constant DC current in the range of from about 2–5 mA. In a well established application of iontophoresis, that of enhancing drug delivery through the skin (transdermal iontophoresis), one electrode is positioned over the treatment area and the second electrode is located at a remote site, usually somewhere else on the skin. The return electrode may, for certain applications, be placed elsewhere on the same organ as the iontophoretic delivery electrode. With the present invention the return electrode may be similarly positioned on the skin. The applied potential for iontophoresis will depend upon number of factors, such as the electrode configuration and position on the tissue, the nature and charge characteristics of the molecules to be delivered, and the presence of other ionic species within the polymer matrix and in the tissue extracellular compartments.

As used herein, the term "electroporation" means the temporary creation of holes or aqueous pores in the surface of a cell membrane by an applied electrical potential and through which therapeutic agents may pass into the cell. Electroporation is now widely used in biology, particularly for transfection studies, where plasmids, DNA fragments and other genetic material are introduced into living cells. During electroporation pulsing, molecules which are not normally membrane permeant are able to pass from the extracellular environment into the cells during the period of induced reversible membrane permeabilization. The permeabilized state is caused by the generation of an electrical field in the cell suspension or tissue of sufficient field strength to perturb the cell surface membrane's proteolipid structure. This perturbation (sometimes referred to as dielectric breakdown) is believed to be due to both a is constituent charge separation and the effect of viscoelastic compression forces within the membrane and it's sub-adjacent cytoskeletal structures. The result is a localized membrane thinning. At a critical external field strength, pores or small domains of increased permeability are formed in the membrane proteolipid bi-layer.

During this short period of permeabilization, external agents can rapidly transfer across the surface membrane via these pores and become encapsulated within the cell's cytosol compartment when the membrane reseals. With appropriate electrical parameters for the poration (field strength, pulse width, number of pulses etc), resealing of the membrane begins almost immediately after the pulsing, and little, if any, leakage of cytosol constituents occurs. Providing that a threshold field strength has not been exceeded, the surface membrane can reorganize with a full restoration of it's former structural integrity, receptor status and other functional properties. The resealing rate is temperature sensitive (with an optimum temperature around 37° C.). The temperature depends on the phase transition temperature of lipids in the membrane bi-layer and the capacity of proteins, and other integral membrane constituents, to diff-use laterally within the bi-layer. Too high a field strength can cause membrane breakdown beyond it's capacity to reseal the electropores.

Electrical fields for poration are commonly generated by capacitor discharge power units using pulses of very short (micro to millisecond) time course. Square wave and radio frequency pulses have also been used for cell electroporation. Of the commercially available power supplies suitable for electroporation, the ECM Voltage Generator ECM 600, available from BTX Inc of San Diego Calif., generates an exponential decay pulse which can be adjusted through resistor selection and different capacitor ranges to give pulse lengths in the range microseconds to milliseconds suitable for electroporating living cells. With narrow electrode gap widths such as the 0.1 or 0.2 mm gaps suggested here for the PCB electrode pairs, appropriate field strengths for tissue electroporation are possible (Kvolts/cm) using low, physiologically acceptable input voltages.

To date, most of the literature reports on electroporation have been concerned with cells in suspension and there is little if any background on cells resident in tissues. It has been reported that cells in monolayer culture, simulating an attached epithelium, require lower field strengths for successful poration (as indexed by higher transfection rates) than the same cells in free suspension. Moreover, cells which are in electrical contact or which can communicate by molecular conversation with neighbor cells through junctions can generally be electroporated at lower field strengths than the same cells in which are in a single cell suspension.

Animal cells in suspension can be electroporated with field strengths in the range 0.5 to 7.0 Kvolts/cm and the critical field strength for successful permeabilisation with resealing varies inversely with cell size, at least for cells which are approximately spherical in shape. It is this inverse relationship that allows the application of a field strength sufficient to porate a cell's surface membrane without disruption of the boundary membranes of important intracellular organelles and other structures.

Three preferred patch embodiments are set forth below. These three embodiments each comprise a patch having electrodes in a preselected pattern. The electrodes may be arranged in any pattern. However, the preferred arrangement comprises two electrodes arranged parallel to one another in an interlocking parallel pattern, otherwise referred to as a "meandering path" electrode. Additionally, the patch may include a plurality of slots or small holes passing through the patch.

In a first embodiment, which is shown in FIGS. 1a and 1b, the patch 100 comprises an electrode network 102 having positive and negative electrodes 104, 106 which are attached to the tissue facing surface of a polymer material base 110. The patch 100 may be made from any polymer material 110 that is capable of being attached to the electrodes 102, 104. However, as the preferred uses of the patch 100 include insertion of the patch inside the human body for extended periods of time, preferably, the polymer material 110 comprises a non-toxic and non-degradable material. Preferably, the polymer material base 110 comprises polyimide.

The electrode network 102 preferably comprises a plurality of electrodes 104, 106 arranged in a preselected pattern. The pattern may be any pattern necessary to cause drug delivery using iontophoresis, electroporation, or both. The shape of the tissue to be treated 160 may be used in determining the shape of the electrode network 102 such that the network 102 is arranged in a shape corresponding to the shape of the target tissue to be treated, thereby minimizing delivery of the drug to non-target tissues. However, it has been found that for most uses, the electrode network 102 preferably comprises a meandering path configuration.

The electrodes 102 may be made from any useful electrode material that is non-toxic and non-degradable since, as mentioned above, the patch 100 may be inserted inside the human body for extended periods of time during some treatment protocols. The electrodes 102 may, therefore, be made from a metal, such as copper, gold, platinum, stainless steel, or silver, or even be made of carbon fiber filaments. Preferably, the electrodes 102 comprise copper. The electrodes 102 may be coated with a thin layer of gold after production if desired. Preferably, the electrodes 102 should have a thickness of from about 0.08 to about 0.20 mm. More preferably, the electrodes 102 should have a thickness of from about 0.12 to about 0.14 mm.

As can be seen in FIG. 1b, in a preferred embodiment, the patch 100 is attached to the tissue to be treated. The patch 100 may be placed on the tissue or, preferably, may be sutured to the tissue using means for suturing. These means for suturing may comprise suture points 120 or any other means capable of holding the patch in place on the tissue to be treated for an extended period of time. The means for suturing can be holes in the patch or regions thereof capable of being pierced and held into place by a suture. These suture points 120 allow the device to be implanted on internal tissue and, through the use of rechargeable reservoirs and internal power supplies, remain attached to the tissue for extended periods of time. The polymer base material 110 is attached to the electrode layer 134, preferably copper, using a layer of glue 132 or other adhesive. Preferably, a gold coating 136 is applied to the copper electrode layer 134.

The treatment agent to be applied may be placed on the gold coating 136 using a hydrogel layer 138 which contains the treatment agent. The drug may also be applied directly to the gold coating 136. However, in preferred embodiments, discussed hereafter, a drug reservoir is used.

In a preferred variation of this embodiment, the patch 100, is from about 1–5 cm in diameter. However, the patches may be smaller or larger since the size of the patch may vary as needed depending upon the area of tissue to be treated. The polyimide base material layer 110 preferably has a thickness of about 50 $\mu$m. If used, the glue or adhesive layer 132 preferably has a thickness of about 25 $\mu$m. The copper layer 134 and the gold coating 136 preferably have thicknesses of about 17.5 $\mu$m and 2 $\mu$m, respectively.

In using the present device for iontophoretically enhanced drug delivery, a separate electrode of opposite polarity to the patch electrodes may be used in order to generate the potential gradient across the artery or other body tissue. This electrode is positioned elsewhere on or in the patient's body (usually the skin) and may be attached using any known means, such as ECG conductive jelly. Alternatively, a catheter electrode may be used as the second electrode.

The polarity direction for the network and plate electrodes is selected according to the charge characteristic of the treatment agent to be delivered. Positively charged agents will iontophoretically migrate towards the negatively charged electrode and vice versa.

As previously discussed, while stainless steel wire or other conductive material may be used for the electrodes 102, preferably the electrodes 102 are of a different construction and comprises a series of very narrow and flexible printed circuit board ("PCB") tapes. The electrodes 102 are first constructed on a flat metal sheet, such as copper, gold, platinum, silver or titanium which is attached to a base material. The metal is preferably copper and the base material is preferably a polyimide material. The base and metal sheet are preferably preformed into the preselected pattern. The paired electrode tracks are etched into this plate by a conventional procedure familiar to those skilled in the art of PCB manufacture. The electrodes 102 may be coated with a thin layer of gold after production if desired. This coating is able to prevent oxidation processes occurring on the electrodes which would affect their efficiency.

The commercial procedure for making such conductive tracks is familiar technology to those skilled in the art of integrated circuitry manufacture, minicomputer motherboard production and other forms of micro circuitry instrumentation. The electrodes may be coated with a thin layer of gold after production if desired. This coating is able to prevent oxidation processes occurring on the electrodes which would affect their efficiency.

In a preferred embodiment, there are a plurality of electrodes 102, with each electrode being from about 0.15 to about 0.3 mm wide. More preferably, the electrodes 102 are about 0.2 mm in width. Preferably, the electrodes 102 extend the full depth of the metal sheet, preferably of copper, down to the base material, preferably a polyimide material. The electrode gaps between each pair would be about the width of the electrodes, also about 0.2 mm. However, the distance between the electrodes 102 and the distance between the electrodes 102 and the edge of the PCB plate is preferably about 0.5 mm. However, smaller distances (from about 0.125 to about 0.2 mm) are possible in a batch production protocol.

In a second embodiment of the present invention, which is shown in FIGS. 2a and 2b, the patch 200 is similar to the patch of the first embodiment. However, for this embodiment, the patch 200 includes a semi-permeable membrane 240. The patch 200 comprises an electrode network 202 having positive and negative electrodes 204, 206 which are attached to the tissue facing (lower) surface of a polymer patch base material 210, preferably polyimide. Additionally, the patch 200 includes a plurality of slots 212 passing from the opposite reservoir facing surface through the polymer base material 210 to the tissue facing surface. The slots allow a drug reservoir 250 or other means of delivering a drug to be placed on the patch 200. The reservoir 250 is in fluid communication with the tissue facing side of the patch 200 via the semi-permeable membrane and is used to deliver the treatment agent to the tissue to be treated 260. By using a reservoir 250 located above the base material 210 and the electrode network 202, the reservoir 250 may be recharged with medicament, or separate medicaments may be added, without removing the patch 200 from the tissue. Recharging of the reservoir may be carried out via a fine catheter (not shown) leading from a supply outside the body, passing through the skin to connect with the inlet tube of the patch reservoir. This is extremely advantageous when the patch has been attached and enclosed within an individual for extended treatment protocols. As such, the patch 200 may also include suture points 220 which allow the patch to be attached to the tissue to be treated 260 in a secure manner for extended periods of time.

As mentioned, this embodiment includes a semi-permeable membrane 240 allowing fluid communication between the reservoir 250 and the electrodes 200. This may be achieved as shown by slots 212 in the membrane 240. By using slots 212 and a semi-permeable membrane 240 between the patch electrode 200 and the reservoir 250, it is possible to control the rate of permeation of the drug to the electrode 200 or even to create selective passage of the drug through only a small portion of the membrane 240, thereby allowing different sized and shaped target tissue 260 without applying the drug to non-target tissue.

As with the first embodiment, a preferred embodiment of the patch 200 includes a plurality of electrodes 202, with each electrode being from about 0.15 to about 0.3 mm wide. More preferably, the electrodes 202 are about 0.2 mm in width. Preferably, the electrodes 202 extend the full depth of the metal sheet, preferably copper, down to the base material, preferably a polyimide. The electrode gaps between each pair can be about the width of the electrodes, from about 0.15 to about 0.3 mm, also about 0.2 mm. Also, the electrodes 202 preferably comprise a series of very narrow and flexible printed circuit board ("PCB") tapes. The electrodes 202 can be first constructed on a flat metal sheet, such as copper, which is attached to a base material. The base material is preferably a polyimide material.

In a third embodiment of the present invention, as shown in FIGS. 3a and 3b, the patch 300 is very similar to the patch of the second embodiment, except that instead of slots, the patch 300 includes a perforated polyimide base 310 with small orifices 315 between the electrode network 302. The patch 300 is preferably from about 1–5 cm in diameter and includes positive and negative electrodes 304, 306. The patch 300 may be attached to the target tissue 360 using suture points 320. Lastly, the patch may include a semi-permeable membrane 340 located between the patch 300 and a drug reservoir 350. As discussed previously, the orifices 315 operate in a similar manner as the slots by controlling the rate of permeation of the drug and/or by allowing selective permeation of the drug such that only target tissue is treated. Also as discussed previously, using a reservoir 350 located above the base material 310 and the electrode network 302, the reservoir 350 may be recharged with medicament without removing the patch 300 from the tissue In use, the patch may be connected to a suitable pulse generator. The generator sends pulses to the tissue across narrow electrode gaps. These pulses are preferably of a field strength (volts/cm.) in the range used for cell electroporation an having only low and physiologically acceptable peak input voltages. For example a peak input voltage of say 40 volts with electrode gap widths of 0.2 mm would give a field strength of 2.0 kV/cm. (i.e. 50×30 volts). A reduction in electrode gap width would give a corresponding increase in field strength.

Additionally, the patch may be modified such that power is only delivered to a portion of the electrodes. In this manner, only the portion of the target tissues that required treatment would be treated.

The electrodes in the device may be switched to single polarity for use with an external plate electrode for iontophoresis or switched to electrode pairs of opposite polarity for electroporation. In the latter procedure, an external plate electrode is not required and is disconnected at the power supply.

Iontophoretically enhanced delivery requires that the therapeutic agent carry a net charge under physiological conditions whereas electroporation alone would be used for delivering treatment agents that are not sufficiently ionized to iontophorese well into tissues. Electroporation may also be the preferred strategy for enhancing localized cellular targeting of a systemically administered agent such as in tumor chemotherapy.

The combined use of pre-iontophoresis followed by electroporation may be appropriate for local delivery of drugs that penetrate intact cell membranes poorly or not at all or where a high extracellular concentration is required for rapid diffusion through the transient electropores to an intracellular target.

The patch may be used, as discussed above, in a combined iontophoresis/electroporation process, such as for an angioplasty procedure. First, a period of continuous or pulsed iontophoresis would first be applied to enhance drug migration out of the polymer coating and into the tissue to raise the drug concentration to a sufficiently high level within the tissue extracellular spaces. After iontophoretic delivery, and without removing or repositioning the patch, the electrodes on the patch would be switched from their single polarity to the paired electrode mode in each PCB strip. The target tissue would then be subjected to a series of high field strength, very short time electroporation pulses to transiently electroporate the surface membranes of cells in the target tissue. The drug in the extracellular spaces of the tissue is then able to rapidly diffuse down a concentration gradient through the open cell membrane pores, enter the cell's cytosol compartments for targeting to intracellular structures such as the nucleus, cytoskeletal elements and metabolic or signal transduction pathways. The porated cell membranes would subsequently reseal with full restoration of cell integrity.

The treatment agent may be delivered through the patch using several different embodiments. In one embodiment, which may be used with any of the patch embodiments set forth, the treatment agent is incorporated within a polymer matrix. The treatment agent may then be iontophoretically driven out of this polymer matrix into the adjacent tissue. The polymer matrix preferably has a good drug holding capacity and is sufficiently pliant to be compressed against the tissue when the electrode network is expanded.

With respect to the polymer composition, the term "polymer matrix" as used herein includes synthetic hydrogel polymers with pores or interstices of different sizes and capacities introduced during manufacture, and a variety of synthetic elastomers and naturally occurring polymeric materials known to those skilled in the art. The drug or therapeutic agent can be incorporated in the matrix either during polymer production or added after coating or molding of the polymer into the desired shape. Additionally, many of a number of different polymeric materials and methods of fabrication may be used to form the polymer matrices used in the present invention.

In a second embodiment, the patch-based device includes a reservoir chamber. The reservoir chamber is designed to hold a treatment agent. Additionally, means are provided for driving the treatment agent from the reservoir such that the agent is then capable of being driven into the target tissues using iontophoresis, electroporation, or both. The reservoir is preferably located above the patch in fluid communication with the electrodes such that the reservoir may be refilled or a separate medicament added without displacing the patch, thereby permitting the patch to be used for extended periods of time.

In a third embodiment, biodegradable microparticles or liposomes may be used to encapsulate the drug or treatment agent. These drug-laden carrier vehicles may be placed between the patch and the tissue to be treated. The liposomes may be electropermeabilized or the microspheres fragmented by applied electroporation pulses. Delivery of drug into the tissue is then enhanced by the use of iontophoretic and/or electroporation pulsing.

In a fourth embodiment hollow microspheres with encapsulated therapeutic agent or agents may be housed in the reservoir mounted on the back of the patch. Microspheres suitable in the present invention include those sold under the name BiSphere™ available from POINT Biomedical (San Carlos, Calif.). These are 3–6 microns in diameter, have a double walled construction and hollow interior to hold the drug. They can be manufactured to be variably acoustically tunable so that they will fragment at different ultrasonic energy levels releasing their drug cargo into the patch reservoir. The soluble drug will pass through the slots or small orifices in the patch polyamide structure (which retains the microsphere debris) to be available for electrically enhanced delivery to the target tissue.

Ultrasonic fragmentation can be effected by a probe outside the body. Thus a sequence of segmental doses can be delivered to the target tissue without need for reservoir recharging. If the power supply for iontophoresis and electroporation is also arranged to be implantable, and perhaps remotely switched on and off via an external magnetically operated a reed switch, then the complete unit can be placed in the body adjacent to the treatment site where it can remain throughout a treatment program.

For some treatment protocols, it may be desired to treat the target tissue over an extended period of time and with a variety of different treatment agents. For these protocols, the patch may be placed on the target tissue and sutured thereto. After the patch had been placed, the individual can have a small tubular portion and any electrical driving means for the patch located outside of the body. The tubular means would be connected to the reservoir while the driving means would enable the patch to be used for iontophoresis, electroporation or both. As needed, treatment agent could be delivered through the tube into the reservoir and then out into the target tissue. The use of the tube would permit extended treatment times and would even permit different treatment agents to be used in the same target tissue.

Alternatively, instead of having external driving means, the patch may include an internal power supply, such as a battery, which would provide the driving means to enable the patch to be used for iontophoresis, electroporation or both. Use of an internal power supply would enable the patch to be located internally while permitting the individual to move about without the difficulties associated with an external power supply.

The patches of the present invention may be used in many treatment protocols not otherwise available to catheter-based device and, using the reservoir, may be used with liquid treatment agents that otherwise would drift away from the target tissue. The patches may be used to deliver treatment agents such as, but not limited to, angiogenesis compounds, antineoplastic agents, anti-angiogenesis compounds and antiarrythmic agents.

We claim:

1. A patch-based device for enhancing the local delivery of a treatment agent into target tissues comprising:

a patch base having a tissue facing surface and a reservoir facing surface;

an electrode network comprising a plurality of electrodes arranged in a spaced parallel pattern on the tissue facing surface of the patch base; and a treatment agent reservoir on the reservoir facing surface of the patch base in fluid communication with the tissue facing surface of the patch base and the electrode network.

2. The patch-based device of claim 1, wherein the device further comprises a recharging tube connected to the reservoir such that a treatment agent may be delivered through the tube, into the reservoir and from the reservoir through the patch base and into the target tissues.

3. The patch-based device of claim 1, wherein the electrodes have a thickness of from about 0.10 to about 0.20 mm.

4. The patch-based device of claim 1, wherein the electrodes are from about 0.15 to about 0.3 mm in width.

5. The patch-based device of claim 1, wherein the electrodes are spaced apart from about 0.15 to about 0.3 mm.

6. The patch-based device of claim 1, wherein the electrodes comprise a plurality of printed circuit board strips.

7. The patch-based device of claim 6, wherein the printed circuit board strips comprise a metal layer attached to an electrode base material.

8. The patch-based device of claim 7, wherein the metal layer is copper.

9. The patch-based device of claim 7, wherein the electrode base material is polyimide.

10. The patch-based device of claim 1, wherein fluid communication is facilitated by a semi-permeable membrane on the patch base having perforations therein.

11. The patch-based device of claim 1, wherein the patch is pre-disposed with means for suturing the patch to the target tissue.

12. The patch-based device of claim 1, wherein the reservoir is rechargeable.

13. The patch-based device of claim 1, wherein the parallel pattern is a meandering path configuration.

14. A method of delivering a treatment agent into target tissues of a bodily vessicle comprising:

applying a treatment agent to the reservoir of the patch-based device of claim 1;

placing the patch on the target tissues to be treated; and applying means for driving the treatment agent from the electrode network into the tissue walls.

15. The method of claim 14, wherein the means for driving the treatment agent from the electrode network into the target tissues comprise iontophoretic means.

16. The method of claim 15, further comprising electroporation means to further drive the treatment agent from the electrode network into the target tissues.

17. The method of claim 14, wherein the means for driving the treatment agent from the electrode network into the target tissues comprise electroporation means.

18. The method of claim 14, wherein the treatment agent is placed in a reservoir and the patch is implanted on the target tissue, and wherein the device further comprises a recharging tube connected to the reservoir such that treatment agent may be delivered through the tube, into the reservoir and from the reservoir through the patch base and into the target tissues.

19. The method of claim 14, wherein the treatment agent is encapsulated within biodegradable microparticles or liposomes that are placed in an area between the target tissue and the patch such that the treatment agent can be made available for electrically enhanced delivery by electroporation of the microparticles or liposomes.

20. The method of claim 14, wherein the treatment agent is encapsulated within ultrasonically labile microspheres; and the later step of applying ultrasonic energy to fragment the microspheres to release the treatment agent which then passes from the reservoir to the target tissue where it is delivered to the target tissue using electrically enhanced delivery.

* * * * *

UNITED STATES PATENT AND TRADEMARK OFFICE
CERTIFICATE OF CORRECTION

PATENT NO.   : 6,424,862 B1
DATED        : July 23, 2002
INVENTOR(S)  : Charles L. Brown III et al.

It is certified that error appears in the above-identified patent and that said Letters Patent is hereby corrected as shown below:

<u>Title page,</u>
Item [60], please add -- [60] Related U.S. Application Data Provisional application No. 60/119,749, filed on February 10, 1999 --.

Signed and Sealed this

Eleventh Day of February, 2003

JAMES E. ROGAN
*Director of the United States Patent and Trademark Office*